(12) United States Patent
Kamal et al.

(10) Patent No.: US 8,383,618 B2
(45) Date of Patent: Feb. 26, 2013

(54) C2-FLUORO SUBSTITUTED PIPERAZINE LINKED PYRROLO[2,1-C][1,4] BENZODIAZEPINE DIMERS AND A PROCESS FOR THE PREPARATION THEREOF

(75) Inventors: Ahmed Kamal, Andhra Pradesh (IN); Rajender, Andhra Pradesh (IN); Metuku Kashireddy, Andhra Pradesh (IN); Gorre Balakishan, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 7 days.

(21) Appl. No.: 12/921,841

(22) PCT Filed: Oct. 31, 2008

(86) PCT No.: PCT/IN2008/000715
§ 371 (c)(1),
(2), (4) Date: Apr. 26, 2011

(87) PCT Pub. No.: WO2009/113084
PCT Pub. Date: Sep. 17, 2009

(65) Prior Publication Data
US 2011/0190275 A1 Aug. 4, 2011

(30) Foreign Application Priority Data
Mar. 11, 2008 (IN) .............................. 608/DEL/2008

(51) Int. Cl.
C07D 487/04 (2006.01)
C07D 519/00 (2006.01)
A61K 31/5517 (2006.01)
A61P 35/00 (2006.01)

(52) U.S. Cl. ........................................ 514/220; 540/496
(58) Field of Classification Search .................. 540/496; 514/220
See application file for complete search history.

(56) References Cited

U.S. PATENT DOCUMENTS
7,173,026 B2 2/2007 Kamal et al.
7,465,724 B2 12/2008 Kamal et al.

FOREIGN PATENT DOCUMENTS
WO 2004/087716 A1 10/2004
WO 2005/063758 A1 7/2005
WO 2007/105045 A1 9/2007

OTHER PUBLICATIONS

S. Kunimoto, et al; "Mazethramycin, A New Member of Anthramycin Group Antibiotics", The Journal of Antibiotics, vol. 33, No. 6, Jun. 1980, pp. 665-667.

Kurt W. Kohn, et al; "Reaction of Anthramycin with Deoxyribonucleic Acid", Journal of Molecular Biology, vol. 51, Issue 3, Aug. 14, 1970, pp. 551-572.

Lawrence H. Hurley, et al; "Pyrrolo(1,4)Benzodiazepine Antitumor Antibiotics in Vitro Interaction of Anthramycin, Sibiromycin and Tomaymycin with DNA Using Specifically Radiolabelled Molecules", Biochimica et Biophysica Acta, vol. 475 (1977), pp. 521-535.

David J. Kaplan, et al; "Anthramycin Binding to Deoxyribonucleic Acid-Mitomycin C Complexes Evidence for Drug-Induced Deoxyribonucleic Acid Conformational Change and Cooperativity in Mitomycin C Binding", Biochemistry, Dec. 22, 1981; vol. 20, Issue 26; pp. 7572-7580.

David E. Thurston, et al; "Synthesis of Sequence-Selective C8-Linked Pyrrolo[2,1-c] [1,4]benzodiazepine DNA Interstrand Cross-Linking Agents", The Journal of Organic Chemistry, Nov. 15, 1996, vol. 61, Issue 23, pp. 8141-8147.

Stephen J. Gregson, et al; "Design, Synthesis, and Evaluation of a Novel Pyrrolobenzodiazepine DNA-Interactive Agent with Highly Efficient Cross-Linking Ability and Potent Cytotoxicity", Journal of Medicinal Chemistry; Mar. 1, 2001, vol. 44, Issue 5, pp. 737-748.

Ahmed Kamal, et al; "Design, Synthesis, and Evaluation of New Noncross-Linking Pyrrolobenzodiazepine Dimers with Efficient DNA Binding Ability and Potent Antitumor Activity", Journal of Medicinal Chemistry, Oct. 10, 2002; vol. 45, Issue 21, pp. 4679-4688.

Ahmed Kamal, et al; "Synthesis of Novel C2 and C2-C8 Linked Pyrrolo[2,1-c][1,4]benzodiazepine-naphthalimide Hybrids as DNA-Binding Agents", Bioorganic & Medicinal Chemistry Letters, vol. 13, Issue 20, pp. 3577-3581; Oct. 20, 2003.

(Continued)

*Primary Examiner* — Bruck Kifle
(74) *Attorney, Agent, or Firm* — Ladas & Parry LLP

(57) ABSTRACT

The present invention provides a compounds of general formula IXa-d, useful as potential antitumour agents and pharmaceutical composition comprising these compounds exhibits binding affinity with calf thymus (CT) DNA at a molar ratio of 1:5 in aqueous sodium phosphate buffer at pH of 7.00. The present invention further provides a process for the preparation of C2-Fluoro substituted piperazine linked pyrrolo[2,1c][1-4], benzodiazepine of formula (IX).

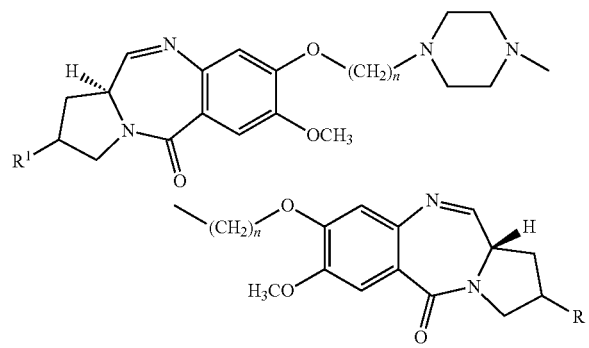

15 Claims, No Drawings

OTHER PUBLICATIONS

Ian A. O'Neil, et al; "The synthesis and biological activity of C2-fluorinated pyrrolo[2,1-c][1,4]benzodiazepines", Tetrahedron Letters, vol. 44, Aug. 14, 2003, pp. 7809-7812.

Ahmed Kamal, et al; "DNA binding potentional and cytotoxicity of newly designed pyrrolobenzodiazepine dimers linked through a piperazine side-armed-alkane spacer", Bioorganic & Medicinal Chemistry, Elsevier Science Ltd, GB, vol. 14, No. 2, Jan. 15, 2006, pp. 285-394, XP025132916, ISSN: 0968-0896 [retrieved on Jan. 15, 2006] p. 386; figure 1; compounds 4, 6A-6D; p. 388; tables 2,3, p. 389; figure 3.

International Search Report; mailed Mar. 3, 2009; PCT/IN2008/000715.

C2-FLUORO SUBSTITUTED PIPERAZINE LINKED PYRROLO[2,1-C][1,4] BENZODIAZEPINE DIMERS AND A PROCESS FOR THE PREPARATION THEREOF

FIELD OF THE INVENTION

The present invention relates to C2-Fluoro substituted piperazine linked pyrrolo2,1-c][1,4]benzodiazepine dimers of formula IX

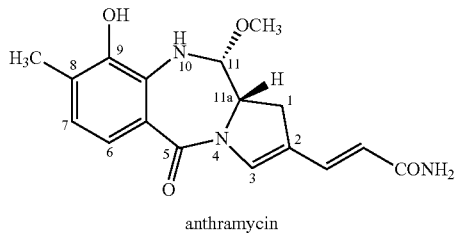

anthramycin

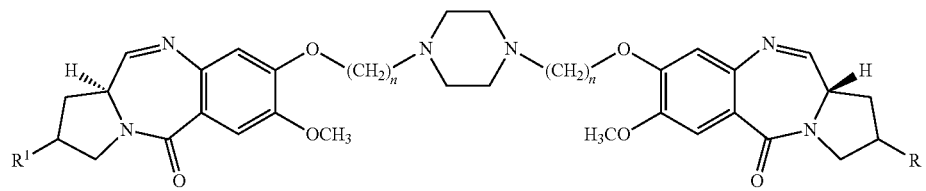

Formula IX

R=R¹=F or F₂; n= 3-10

The present invention also relates to a process for the preparation of pyrrolo[2,1-c][1,4]benzodiazepine. More particularly, it provides a process for the preparation of 1,1'-{([(bisalkane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one], and 1,1'-{[(bisalkane-1,N-diyl)piperazine]dioxy}bis(11aS)-2-2-difluoro-7-methoxy-1,2,3,11a-tetrahydro-5H-pyrrolo[2,1-c][1,4]benzodiazepine-5-one, with aliphatic chain length variations (n=3-10) for the compounds and it also describes the DNA-binding ability and anticancer (antitumour) activity.

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.,* 1980, 33, 665.; Kohn, K. W. and Speous, C. L. *J. Mol. Biol.,* 1970, 51, 551.; Hurley, L. H.; Gairpla, C. and Zmijewski, M. *Biochem. Biophys. Acta.* 1977, 475, 521.; Kaplan, D. J. and Hurley, L. H. *Biochemistry,* 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S. and Hurley, L. H. *J. Org. Chem.* 1996, 61, 8141).

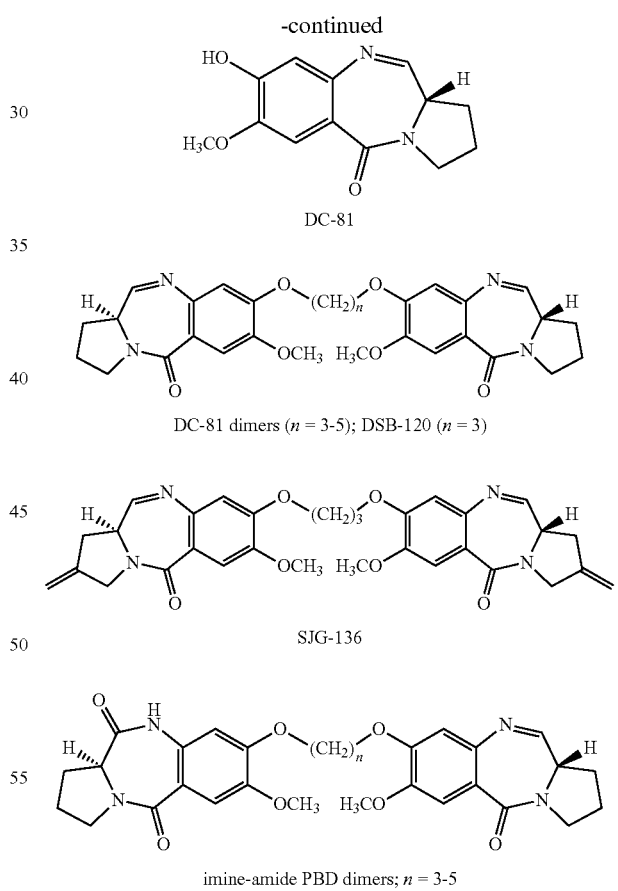

DC-81

DC-81 dimers (n = 3-5); DSB-120 (n = 3)

SJG-136 imine-amide PBD dimers; n = 3-5

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679). Recently, some new pyrrolobenzodiazepine (PBD) hybrids have been synthesized that have significant DNA binding ability and potent antitumour activity (Kamal, A.; Srinivas, O.; Ramulu, P.; Ramesh, G.; Kumar, P. P. *Bioorg. Med. Chem. Lett.* 2003, 13, 3577). Recently mono-fluoro and difluoro pyrrolo[2,1-c][1,4]benzodiazepines have been synthesized (O'Neil, A.; Thomoson. S.; Kalindjian, S. B.; Jenkins, T. C.; *Tetrahedron Lett.* 2003, 44, 7809).

Naturally occurring pyrrolo[2,1-c][1,4]benzodiazepines belong to a group of antitumour antibiotics derived from *Streptomyces* species. Recently, there is much impetus for the PBD systems as they can recognize and bind to specific sequence of DNA. Examples of naturally occurring PBDs include anthramycin, DC-81, tomaymycin, sibiromycin and neothramycin.

However, the clinical efficacy for these antibiotics is hindered by several limitations, such as poor water solubility, cardio toxicity, development of drug resistance and metabolic inactivation.

OBJECTIVES OF THE INVENTION

The main object of the present invention is to provide C2-Fluoro substituted piperazine linked pyrrolo[2,1-c][1,4] benzodiazepines useful as antitumour agents.

Yet another object of this invention is to provide pharmaceutical compositions comprising C2-Fluoro substituted piperazine linked pyrrolo[2,1-c][1,4]benzodiazepines useful as anti-cancer agents.

Yet another object of this present invention is to provide C2-Fluoro substituted piperazine linked pyrrolo[2,1-c][1,4] benzodiazepines as potential DNA-binding agents.

Yet another object of this invention is to provide a process for the preparation of C2-Fluoro substituted piperazine linked pyrrolo[2,1-c][1,4]benzodiazepines.

SUMMARY OF THE INVENTION

According, the present invention provides C2-Fluoro substituted piperazine linked pyrrolo[2,1c][1,4]benzo-diazepine of formula IX.

In an embodiment of the present invention the compound C2-Fluoro substituted piperazine linked pyrrolo[2,1-c][1,4] benzodiazepine of general formula IX is represented by the group of following compounds:

1,1'-{[(bispropane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one] (IXa);

1,1'-{[(bisbutane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one] (IXb);

1,1'-{[(bispentane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one] (IXc);

1,1'-{[(bispropane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one] (IXd);

1,1'-{[(bisbutane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one] (IXe) and 1,1'-{[(bispentane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one] (IXf).

In yet another embodiment the compound C2-Fluoro substituted piperazine linked pyrrolo[2,1-c][1,4]benzodiazepine dimers, exhibits an in vitro anticancer/antitumour activity against human cancer cell lines selected from the group of lung, colon, breast, ovarian, leukemia, Renal, Melanoma, Prostate and CNS cell lines In yet another embodiment the compound C2-Fluoro substituted piperazine linked pyrrolo[2,1-c][1,4]benzodiazepine dimers (IXa-f) exhibits binding affinity with calf thymus (CT) DNA at a molar ratio of about 1:5 in aqueous sodium phosphate buffer at pH of 7.00.

The preset invention further provides a process for the preparation of C2-Fluoro substituted piperazine linked pyrrolo[2,1-c][1,4]benzodiazepine formula IX Formula IX

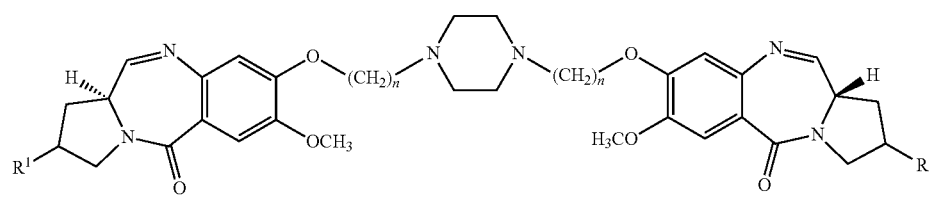

wherein R = R¹ = F or F₂; n = 3-10

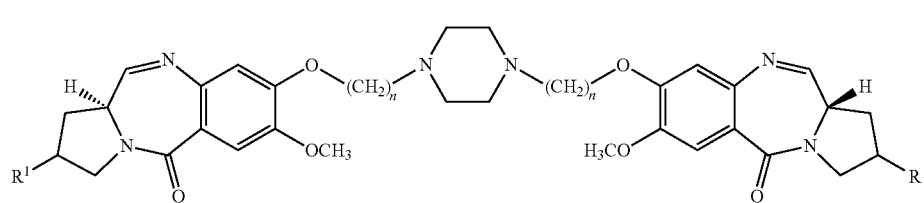

Formula IX wherein R=R¹=F or F₂; n= 3-10 and the said process comprising the step of:
(a) Preparing (2S)—N-(4-hydroxy-5-methoxy-2-nitrobenzoyl)4,fluorinated-pyrrolidine-2-carboxaldehydediethylthioacetal of formula IV by known method.

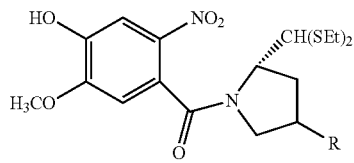

Formula IV

R = F or F₂

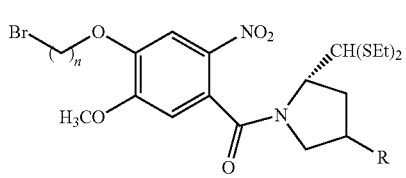

Formula V

R = F or F₂   n = 3-10

(c) reacting the compound of formula V obtained in step (b) with piperazine of formula VI in a dry aprotic water miscible organic solvent, in the presence of mild inorganic base, under reflux, for a period of 45-48 hours, followed by pouring the resultant reaction mixture on to the water and extracting and purifying the resultant crude product by known method to obtain the compound 1,1'-{[(bisalkane-1,N-diyl)piperazine]dioxy}bis(11aS)-2-fluorinated-7-methoxy-2-nitrobenzoylpyrrolidin-2-carboxaldehydediethylthioacetal] of formula VII (d) reducing the compound of formula VII obtained in step (c) with $SnCl_2 \cdot 2H_2O$ in an organic solvent, under reflux, for a period of 1-2 hours, at a pH of 8 in the presence of saturated alkalibicorbonate solution, followed by extraction with an organic solvent and drying the resultant organic phase over $Na_2SO_4$ and evaporating the solvent under vacuum to obtain the resultant compound. 1,1'-{[(bisalkane-1,N-diyl)

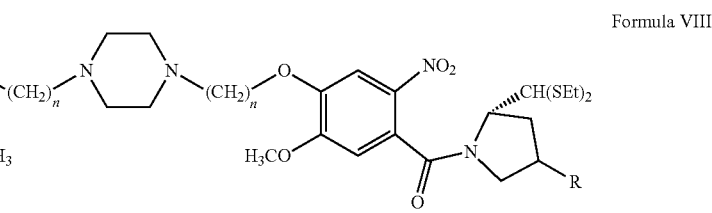

Formula VIII wherein R=R¹=F or F₂; n= 3-10

(b) reacting the compound of formula IV obtained in step (a) with dibromoalkane in a dry aprotic water miscible organic solvent, in the presence of mild inorganic base, under reflux, for a period up to 48 hours, purifying the resultant crude product by known method to obtain the compound of (2S)—N44-n-bromoalkoxy)-5-methoxy-2-nitrobenzoyl)-4,fluorinated-pyrrolidine-2-carboxaldehydediethylthioacetal of formula V.

piperazine]dioxy}bis(11aS)-2-fluorinated-7-methoxy-2-amino benzoylpyrrolidin-2-carboxaldehyddiethylthioacetal] of formula VIII.

In yet another embodiment the compound of formula VIII obtained in step (d) is selected from the group consisting of Formula VIII

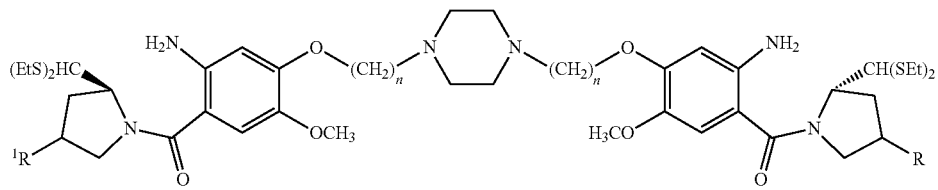

wherein R=R¹=F or F₂; n= 3-10

(e) reacting the compound of formula VIII with mercurous chloride and calcium carbonate in the presence of an aqueous organic solvent wherein organic solvent to water ratio is about 4:1, under stirring, at a temperature of 25-30° C., for a period of about 12 hours, followed by the evaporation of organic layer to obtain the crude residue and purifying the residue by known method to obtain the desired product of 1,1'-{[(bisalkane-1,N-diyl)piperazine]dioxy}bis[(11aS)-2-fluorinated-7-methoxy-1,2,3,11a-tetra-hydro-5H-pyrrolo[2,1-c][1,4]benzodiazepine-5-one], of formula XI.

1,1'-{[(bispropane-1,N-diyl)piperazine]dioxy}bis(11aS)-2-fluoro-7-methoxy-2-aminobenzoylpyrrolidin-2-carboxaldehydediethylthioacetal] (VIIIa);

1,1'-{[(bisbutane-1,N-diyl)piperazine]dioxy}bis(11aS)-2-fluoro-7-methoxy-2-aminobenzoylpyrrolidin-2-carboxaldehydediethylthioacetal] (VIIIb);

1,1'-{[(bispentane-1,N-diyl)piperazine]dioxy}bis(11aS)-2-fluoro-7-methoxy-2-aminobenzoylpyrrolidin-2-carboxaldehydediethylthioacetal] (VIIIc);

Formula IX

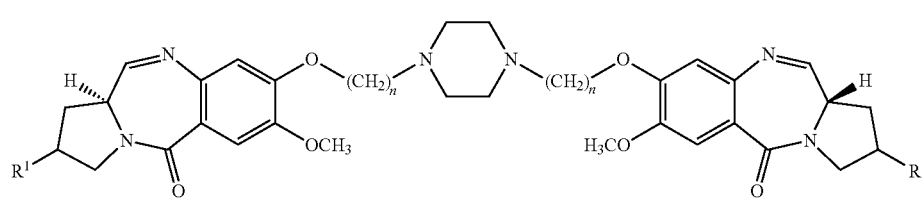

wherein R=R¹=F or F₂; n= 3-10

In yet another embodiment the dibromoalkane used in step (a) is selected from the group consisting of 1,3-dibromopropane, 1,4-dibrombutane and 1,5-dibromopantane.

In yet another embodiment the dry organic solvent used in step (b) and (c) is selected from acetone, acetonitrile and DMF.

In yet another embodiment the mild inorganic base used in step (b) and (c) is selected from $K_2CO_3$, $BaCO_3$ and $CsCO_3$.

In yet another embodiment the compound of formula VII used in step (c) is selected from the group consisting of 1,1'-{[(bispropane-1,N-diyl)piperazine]dioxy}bis(11aS)-2-fluoro-7-methoxy-2-nitrobenzoyl pyrrolidin-2-carboxaldehydediethylthioacetal] (VIIa);

1,1'-{[(bisbutane-1,N-diyl)piperazine]dioxy}bis(11aS)-2-fluoro-7-methoxy-2-nitrobenzoylpyrrolidin-2-carboxaldehydediethylthioacetal] (VIIb);

1,1'-{[(bispentane-1,N-diyl)piperazine]dioxy}bis(11aS)-2-fluoro-7-methoxy-2-nitrobenzoylpyrrolidin-2-carboxaldehydediethylthioacetal] (VIIc);

1,1'-{[(bispropane-1,N-diyl)piperazine]dioxy}bis(11aS)-2-2-difluoro-7-methoxy-2-nitrobenzoylpyrrolidin-2-carboxaldehydediethylthioacetal] (VIId);

1,1'-{[(bisbutane-1,N-diyl)piperazine]dioxy}bis(11aS)-2-2-difluoro-7-methoxy-2-nitrobenzoylpyrrolidin-2-carboxaldehydediethylthioacetal] (VIIe) and 1,1'-{[(bispentane-1,N-diyl)piperazine]dioxy}bis(11aS)-2-2-difluoro-7-methoxy-2-nitrobenzoylpyrrolidin-2-carboxaldehydediethylthioacetal] (VIIf).

1,1'-{[(bispropane-1,N-diyl)piperazine]dioxy}bis(11aS)-2-fluoro-7-methoxy-2-aminobenzoylpyrrolidin-2-carboxaldehydediethylthioacetal] (VIIId);

1,1'-{[(bisbutane-1,N-diyl)piperazine]dioxy}bis(11aS)-2-fluoro-7-methoxy-2-aminobenzoylpyrrolidin-2-carboxaldehydediethylthioacetal] (VIIIe) and 1,1'-{[(bispentane-1,N-diyl)piperazine]dioxy}bis(11aS)-2-fluoro-7-methoxy-2-aminobenzoylpyrrolidin-2-carboxaldehydediethylthioacetal] (VIIIf).

In yet another embodiment the organic solvent used in step (d) are ethyl acetate, chloroform and methanol.

In yet another embodiment the alkalibicorbonate used in step (d) is sodiumbicorbonate.

In yet another embodiment the organic solvent used in step (d) is methanol.

In yet another embodiment the organic solvent used in step (e) is acetonitrile.

In yet another embodiment the compound 1,1'-{[(bisalkane-1,N-diyl)piperazine]dioxy}bis[(11aS)-2-fluorinated-7-methoxy-1,2,3,11a-tetrahydro-5H-pyrrolo[2,1-c][1,4]benzodiazepine-5-one], of formula XI obtained in step (e) is represented by a group of following compounds:

1,1'-{[(bispropane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one] (IXa);

1,1'-{[(bisbutane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one] (IXb);

1,1'-{[(bispentane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one] (IXc);

1,1'-{[(bispropane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one] (IXd);

1,1'-{[(bisbutane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one](IXe)

And 1,1'-{[(bispentane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one] (IXf).

In still another embodiment A pharmaceutical composition useful as anti tumor agent comprising an effective amount of one or more analogues 1,1'-{[(bisalkane-1,N-diyl)piperazine]dioxy}bis[(11aS)-2-fluoro-7-methoxy-1,2,3,-11a-tetrahydro-5H-pyrrolo[2,1-c][1,4]benzodiazepine-5-one] or 1,1'-{[(bisalkane-1,N-diyl)piperazine]bis(11aS)-2-2-difluoro-7-methoxy-1,2,3,11a-tetrahydro-5H-pyrrolo[2,1-c][1,4]benzodiazepine-5-one optionally along with pharmaceutically acceptable additives.

DETAILED DESCRIPTION OF THE INVENTION

The present invention provides a process for the preparation of C2-Fluoro substituted piperazine linked pyrrolo[2,1-c][1,4]benzodiazepines of formula (IXa-f) of the drawing accompanying the specification where n is 3 to 1.0 which comprises: methyl(2S)—N-[4-benzyloxy-5-methoxy-2-nitrobenzoyl]-4-fluorinatedpyrrolidine-2-carbonate of formula I was reduced with DIBAL-H in presence of organic solvent like $CH_2Cl_2$ cooled to $-78°$ C. for a period of 45 min isolating methyl (2S)—N-[4-benzyloxy-5-methoxy-2-nitrobenzoyl]-4-fluorinatedpyrrolidine-2-carboxaldehyde II by conventional methods, protecting the above compound of formula II with EtSH in presence of organic solvent at room temperature isolating the methyl(2S)—N-[4-benzyloxy-5-methoxy-2-nitrobenzoyl]-4-fluorinatedpyrrolidine-2-carboxaldehydediethylthioacetal III by known methods, reacting the above said thio compound of formula III with known debenzylating agents in a conventional manner to give (2S)—N-[4-hydroxy-5-methoxy-2-nitrobenzoyl]-4-fluorinatedpyrrolidine-2-carboxaldehydediethylthioacetal of formula IV. Accordingly, the present process provides a process for preparation for C2-Fluoro substituted piperazine linked pyrrolo[2,1-c][1,4]benzodiazepines of formula of the drawing accompanying the specification where n is 3 to 10 which comprises: reacting (2S)—N-[4-hydroxy-5-methoxy-2-nitrobenzoyl]-4-fluorinatedpyrrolidine-2-carboxaldehydediethylthioacetal of formula IV dibromoalkanes in an aprotic water miscible organic solvent like acetone, acetonitrile, THF, and DMF in presence of a mild inorganic bases like $K_2CO_3$, $CsCO_3$, and $BaCO_3$ upto refluxing temperature for a period upto 48 hours, isolating (2S)—N-[4-(n-bromoalkoxy)-5-methoxy-2-nitrobenzoyl]-4-fluorinatedpyrrolidine-2-carboxaldehydediethylthio-acetal of formula V with piperazine of formula VI in presence of mild inorganic bases like $K_2CO_3$, $CsCO_3$, and $BaCO_3$ and in the presence of aprotic water miscible organic solvent up to refluxing for a period of 48 hours isolating 1,1'-{[(bisalkane-1,N-diyl)piperazine]dioxy}bis(11aS)-2-fluorinated-7-methoxy-2-nitrobenzoylpyrrolidin-2-carboxaldehyddiethylthioactal] VII where n is 3 to 10 by conventional method, reducing the above nitro compound of formula VII with $SnCl_2.2H_2O$ in presence of organic solvent upto a reflux temperature, isolating the 1,1'-{[(bisalkane-1,N-diyl)piperazine]dioxy}bis(11aS)-2-fluorinated-7-methoxy-2-aminobenzoylpyrrolidin-2-carboxaldehydediethylthioactal] of where n is 3 to 10 by know methods, reacting the above said amino compound of formula VIII with known deprotecting agent in a conventional manner to give novel 1,1'-{[(bisalkane-1,N-diyl)piperazine]dioxy}bis[(11aS)-2-fluorinated-7-methoxy-1,2,3,11a-tetrahydro-5H-pyrrolo[2,1-c][1,4]benzodiazepine-5-one] of formula IX where in n are as stated above.

The precursor, methyl(2S)—N-[4-benzyloxy-5-methoxy-2-nitrobenzoyl]-4-fluorinatedpyrrolidine-2-carbonate of formula I (intermediate of DC-81) was prepared by literature method (Dc Luca, L.; Giacomelli, G.; Porcheddu, A. *Org. Lett.* 2001, 3, 3041; Demange, L.; Menez, A.; Dugave, C. *Tetrahedron. Lett.* 1998, 39, 1169; Kamal, A.; Reddy, P. S. M. M.; Reddy, D. R. Bioorg. *Med. Chem. Lett.* 2004, 14, 2669; Kamal, A.; Reddy, P. S. M. M.; Reddy, D. R.; Laxman, E.; Murthy, Y. L. N. *Bioorg. Med. Chem. Lett.* 2004, 14, 5699; Thurston, D. E.; Murthy, V. S.; Langley, D. R.; Jones, G. B. *Synthesis,* 1990, 81).

Same representative compound of formula IX present invention are given below 1) 1,1'-{[(bispropane-1,N-diyl)piperazine]dioxy}bis[(11aS)-2-fluoro-7-methoxy 1,2,3,11a-tetrahydro-5H-pyrrolo[2,1-c][1,4]benzodiazepine-5-one]

2) 1,1'-{[(bisbutane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one]

3) 1,1'-{[(bispentane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one]

4) 1,1'-{[(bispropane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one]

5) 1,1'-{[(bisbutane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one]

6) 1,1'-{[(bispentane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one].

These new analogues of pyrrolo[2,1-c][1,4]benzodiazepines dimers substituted at C2-position linked at C8 position through piperazine moiety have shown promising anticancer activity in various cell lines. The molecules synthesized are of immense biological significance with potential sequence selective DNA-binding property. This resulted in design and synthesis of new congeners as illustrated in Scheme 1 and Scheme 2, which comprise:

1. Ether linkage at C-8 position fluoro substituted at C2-position of DC-81 intermediates with piperazine moiety
2. Refluxing the reaction mixture for 24-48 h.
3. Synthesis of C8-linked C2-fluorosubstituted PBD antitumour antibiotic dimer imines.
4. Purification by column chromatography using different solvents like ethyl acetate, hexane, dichloromethane, chloromethane, and methanol.

The process of preparation of new non-cross linking C2-Fluoro substituted piperazine linked pyrrolo[2,1-c][1,4]benzodiazepine is disclosed and claimed in applicant's co-pending application no.

Scheme 1
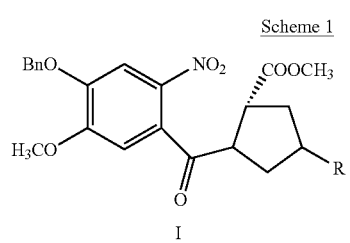
I
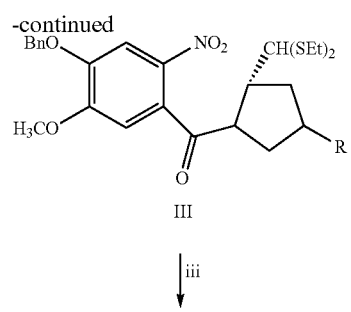
III
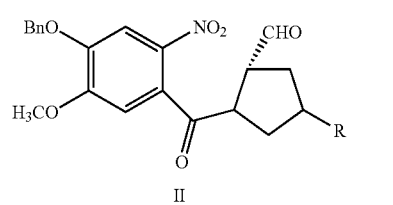
II
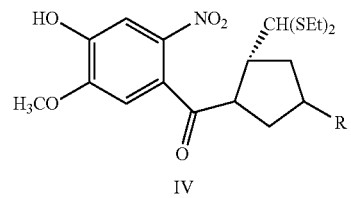
IV
R = F, F₂
Reagents and conditions: (i) DIBAL-H, CH₂Cl₂, -78° C.; (ii) EtSH-TMS-Cl, CH₂Cl₂; (iii) EtSH—BF3OEt, CH₂Cl₂
Scheme 2
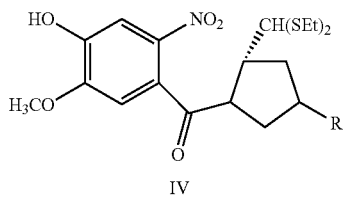
IV
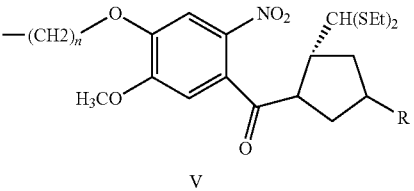
V
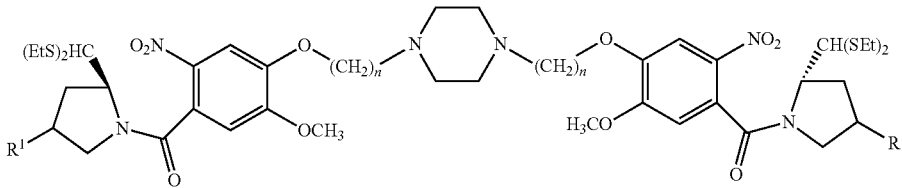
VII
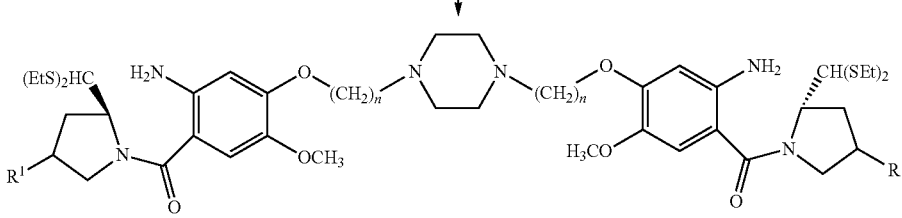
VIII -continued

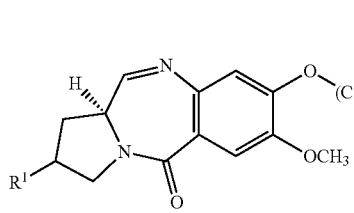 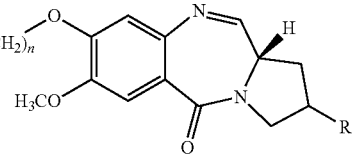

IX i) R = R¹ = F
ii) R = R¹ = F₂
n = 3-10

The following examples are given by way of illustration and therefore should not be construed to the present limit of the scope of invention.

EXAMPLE 1

A solution of (2S)—N-(4-hydroxy-5-methoxy-2-nitrobenzoyl)-4-fluoropyrrolidine-2-carboxaldehydediethylthioacetal IV (418 mg, 1 mmol), 1,3-dibromopropane (0.365 ml, 3 mmol) and $K_2CO_3$ (825 mg, 5 mmol) in dry acetone (40 ml) was refluxed for 48 h. After the completion of reaction as indicated by TLC, EtOAc-hexane (6:4), the reaction mixture was poured on to the water and then extracted with ethylacetate. Evaporation of the organic layer gave the crude product, which was further purified by column chromatography on silica gel eluting with EtOAc-hexane (1:1) gave the pure (2S)—N-[4-(4-bromopropoxy)-5-methoxy-2-nitrobenzoyl)-4-fluoropyrrolidine-2-carboxaldehydediethylthioacetal of formula V (432 mg, 82%).

$^1$H NMR: ($CDCl_3$, 200 MHz): δ 1.31-1.40 (m, 6H), 2.28-2.48 (m, 2H), 2.49-2.64 (m, 2H), 2.68-2.91 (m, 6H), 3.64 (m, 2H), 3.99 (s, 3H), 4.25 (t, 2H, J=6.0), 4.56 (d, 1H, J=6.7), 4.76 (m, 1H), 5.0-5.33 (m, 1H), 6.88 (s, 1H), 7.68 (s, 1H) LCMS: m/z 539.4 ($M^+$+Na).

A solution of (2S)—N-[4-(4-bromopropoxy)-5-methoxy-2-nitrobenzoyl)-4-fluoropyrrolidine-2-carboxaldehydediethylthioacetal of formula V. (539 mg, 1 mmol), piperazine (43 mg, 0.5 mmol) of the formula VI and $K_2CO_3$ (1380 mg, 10 mmol) in dry acetone (20 ml) was refluxed for 48 h. After the completion of reaction as indicated by TLC, EtOAc, the reaction mixture was on to the water and then extracted with ethylacetate. Evaporation of the organic layer gave the crude product, which was further purified by column chromatography on silica gel eluting with EtOAc-hexane (9:1) gave the pure 1,1'-{[(bispropane-1,N-diyl)piperazine]dioxy}bis(11aS)-2-fluoro7-methoxy-2-nitrobenzoylpyrrolidin-2-carboxaldehydediethylthioactal] (441 mg, 82%).

$^1$H NMR ($CDCl_3$, 200 MHz): δ 1.29-1.36 (m, 12H), 2.02-2.11 (m, 4H), 2.46-2.69 (m, 12H), 2.73-2.89 (m, 8H), 3.39-3.62 (m, 4H), 3.93-3.94 (t, 4H), 4.17 (t, 4H), 4.52 (d, 2H, J=6.79), 4.72 (q, 2H, J=6.79), 5.07-5.29 (m, 2H), 6.84 (s, 2H), 7.65 (s, 2H) ESIMS: m/z 1003 ($M^+$).

The 1,1'-{[(bispropane-1,N-diyl)piperazine]dioxy}bis(11aS)-2-fluoro7-methoxy-2-nitrobenzoylpyrrolidin-2-carboxaldehydediethylthioactal]. VII (1004 mg, 1.0 mmol) was dissolved in methanol (20 ml) and added $SnCl_2.2H_2O$ (2.25 mg, 10 mmol) was refluxed for 1.5 h. The reaction mixture was then carefully adjusted to pH 8 with saturated $NaHCO_3$ solution and then extracted with ethyl acetate (3×30 mL). The combined organic phase was dried over $Na_2SO_4$ and evaporated under vacuum to afford the crude. The 1,1-{[(bispropane-1,N-diyl)piperazine]dioxy}bis(11aS)-2-fluoro-7-methoxy-2-aminobenzoylpyrrolidin-2-carboxaldehydediethylthioacetal](803 mg, 80%).

A solution of the 1,1'-{[(bispropane-1,N-diyl)piperazine]dioxy}bis(11aS)-2-fluoro-7-methoxy-2-aminobenzoylpyrrolidin-2-carboxaldehydediethylthioactal] of formula VIII (944 mg, 1 mmol), $HgCl_2$ (1035 mg, 5 mmol) and $CaCO_3$ (500 mg, 5 mmol) in $CH_3CN/H_2O$ (4:1,16 ml) was stirred at room temperature for 12 h. Until TLC (EtOAc), indicates complete loss of starting material. Then organic layer is evaporated in vacuum and the residue is diluted with EtOAc. To this saturated $NaHCO_3$ was added slowly at room temperature and the mixture is filtered through celite and washed with ethylacetate. The filterate is evaporated in vacuum to get crude. 1,1'-{[(bispropane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one], of formula IXa, which was further purified by column chromatography on silica gel eluting first with ethyl acetate to remove traces of mercuric salts and further eluted with $CHCl_3$-methanol (9:1) (613 mg, 65%).

$^1$H NMR ($CDCl_3$, 200 MHz): δ 1.73-2.1 (m, 8H), 2.45-2.76 (m, 8H), 3.46-3.91 (m, 10H), 3.93 (s, 6H), 4.02-4.25 (m, 4H), 5.35-5.48 (dt, 2H), 6.85 (s, 2H), 7.49 (s, 2H), 7.86 (d, 2H, J=3.66 Hz) ESIMS: m/z 695 ($M^+$+1).

EXAMPLE 2

A solution of (2S)—N-(4-hydroxy-5-methoxy-2-nitrobenzoyl)-4-fluoropyrrolidine-2-carboxaldehydediethylthioacetal IV (418 mg, 1 mmol), 1,4-dibromobutane (0.35 ml 3 mmol) and $K_2CO_3$ (675 mg, 5 mmol) in dry acetone (30 ml) was refluxed for 48 h. After the completion of reaction as indicated by TLC, EtOAc-hexan (6:4), the reaction mixture was poured on to the water and then extracted with ethylacetate. Evaporation of the organic layer gave the crude product, which was further purified by column chromatography on silica gel eluting with EtOAc-hexan (1:1) gave the pure (2S)—N-[4-(5-bromobutanoxy)-5-methoxy-2-nitrobenzoyl)-4-fluoropyrrolidine-2-carboxaldehydediethylthioacetal of formula V (355 mg, 85%).

$^1$H NMR: ($CDCl_3$, 200 MHz): δ 1.26-1.43 (m, 6H), 2.01-2.46 (m, 4H), 2.49-2.67 (m, 2H), 2.70-2.95 (m, 6H), 3.58 (m, 2H), 3.99 (s, 3H), 4.25 (t, 2H, J=6.0), 4.55 (d, 1H, J=6.7), 4.73-4.79 (m, 1H), 5.0-5.33 (m, 1H), 6.89 (s, 1H), 7.69 (s, 1H) LCMS: m/z 553 ($M^+$).

A solution of (2S)—N-[4-(5-bromobutanoxy)-5-methoxy-2-nitrobenzoyl)-4-fluoropyrrolidine-2-carboxaldehyde diethyl thioacetal of formula V. (553 mg, 1 mmol), piperazine (43 mg, 0.5 mmol) of the formula VI and $K_2CO_3$ (4014 mg, 10 mmol) in dry acetone (30 ml) was refluxed for 48 h. After the completion of reaction as indicated by TLC, EtOAc, the reaction mixture was on to the water and then extracted with ethylacetate. Evaporation of the organic layer gave the crude product, which was further purified by column chromatography on silica gel eluting with EtOAc-hexane (9:1) gave the pure 1,1'-{[(bisbutane-1,N-diyl)piperazine]dioxy}bis(11aS)-2-fluoro7-methoxy-2-nitrobenzoylpyrrolidin-2-carboxaldehyddiethylthioactal] (447 mg, 81%).

$^1$H NMR (CDCl$_3$, 200 MHz): δ 1.29-1.41 (m, 12H), 1.7-1.97 (m, 8H), 2.33-2.70 (m, 12H), 2.71-2.89 (m, 8H), 3.39-3.66 (m, 4H), 3.90-3.93 (t, 4H), 3.96 (s, 6H), 4.1 (t, 4H), 4.5 (d, 2H, J=7.5), 4.2 (q, 2H, J=6.79), 5.0-5.27 (m, 2H), 6.84 (s, 2H), 7.60 (s, 2H).

The 1,1'-{[(bisbutane-1,N-diyl)piperazine]dioxy}bis(11aS)-2-fluoro7-methoxy-2-nitrobenzoylpyrrolidin-2-carboxaldehydediethylthioactal]. VII (1032 mg, 1.0 mmol) was dissolved in methanol (20 ml) and added SnCl$_2$.2H$_2$O (2025 mg, 10 mmol) was refluxed for 1.5 h. The reaction mixture was then carefully adjusted to pH 8 with saturated NaHCO$_3$ solution and then extracted with ethyl acetate (3×30 mL). The combined organic phase was dried over Na$_2$SO$_4$ and evaporated under vacuum to afford the crude. The 1,1'-{[(bisbutane-1,N-diyl)piperazine]dioxy}bis(11aS)-2-fluoro-7-methoxy-2-aminobenzoylpyrrolidin-2-carboxaldehydediethylthioactal] (825 mg, 80%).

A solution of the 1,1'-{[(bisbutane-1,N-diyl)piperazine] dioxy}bis(11aS)-2-fluoro-7-methoxy-2-aminobenzoylpyrrolidin-2-carboxaldehydediethylthioactal]. of formula VIII (968 mg, 1 mmol), HgCl$_2$ (1035 mg, 5 mot) and CaCO$_3$ (500 mg, 5 mmol) in CH$_3$CN/H$_2$O (4:1,16 ml) was stirred at room temperature for 12 h until TLC (EtOAc), indicates complete loss of starting material. Then organic layer is evaporated in vacuum and the residue is diluted with EtOAc. To this saturated NaHCO3 was added slowly at room temperature and the mixture is filtered through celite and washed with ethylacetate. The filterate is evaporated in vacuum to get crude 1,1'-{[(bisbutane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one], of formula IXb, which was further purified by column chromatography on silica gel eluting first with ethyl acetate to remove traces of mercuric salts and further eluted with CHCl$_3$-methanol (9:1) (580 mg, 60%).

$^1$H NMR (CDCl$_3$, 200 MHz): δ 1.26-1.94 (m, 8H), 2.11-2.47 (m, 4H), 2.59-2.75 (m, 8H), 3.48-3.86 (m, 10H), 3.93 (s, 6H), 4.0-4.25 (m, 4H), 5.27-5.55 (m, 2H), 6.82 (s, 2H), 7.49 (s, 2H), 7.85 (d, 2H, J=4.4 Hz).

EXAMPLE 3

A solution of (2S)—N-(4-hydroxy-5-methoxy-2-nitrobenzoyl)-4-fluoropyrrolidine-2-carboxaldehydediethylthioacetal IV (418 mg, 1 mmol), 1,5-dibromopantane (0.5 ml, 0.5 mmol) and K$_2$CO$_3$ (690 mg, 5 mmol) in dry acetone (40 ml) was refluxed for 48 h. After the completion of reaction as indicated by TLC, EtOAc-hexane (6:4), the reaction mixture was poured on to the water and then extracted with ethylacetate. Evaporation of the organic layer gave the crude product, which was further purified by column chromatography on silica gel eluting with EtOAc-hexane (1:1) gave the pure (2S)—N-[4-(6-bromopentanoxy)-5-methoxy-2-nitrobenzoyl)-4-fluoropyrrolidine-2-carboxaldehydediethylthioacetal of formula V (355 mg, 85%).

$^1$H NMR: (CDCl$_3$ 200 MHz): δ 1.26-1.41 (m, 6H), 1.74-2.0 (m, 4H), 2.35-2.47 (m, 2H), 2.49-2.65 (m, 2H), 2.70-2.92 (m, 6H), 3.58-3.66 (m, 2H), 3.98 (s, 3H), 4.25 (t, 2H, J=6.0), 4.57 (d, 1H, J=6.7), 4.75-4.85 (m, 1H), 5.0-5.34 (m, 1H), 6.88 (s, 1H). 7.70 (s, 1H) LCMS: m/z 567 (M$^+$).

A solution of (2S)—N-[4-(6-bromopentanoxy)-5-methoxy-2-nitrobenzoyl)-4-fluoropyrrolidine-2-carboxaldehydediethylthioacetal of formula V. (567 mg, 1 mmol), piperazine (43 mg, 0.5 mmol) of the formula VI and K$_2$CO$_3$ (1380 mg, 10 mmol) in dry acetone (40 ml) was refluxed for 48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc-hexane (9:1) gave the pure 1,1'-{[(bipentane-1,N-diyl)piperazine]dioxy}bis(11aS)-2-fluoro7-methoxy-2-nitrobenzoylpyrrolidin-2-carboxaldehydediethylthioactal] (453 mg, 80%).

$^1$H NMR (CDCl$_3$, 200 MHz): δ 1.25-1.36 (m, 12H), 1.39-1.89 (m, 12H), 2.25-2.61 (m, 12H), 2.70-2.86 (m, 8H), 3.39-3.63 (m, 4H), 3.96 (s, 6H), 4.0 (t, 4H), 4.12 (t, 4H), 4.54 (d, 2H, J=6.79), 4.75 (q, 2H, J=6.0), 5.0-5.3 (m, 2H), 6.84 (s, 2H), 7.62 (s, 2H).

The 1,1'-{[(bipentane-1,N-diyl)piperazine]dioxy}bis(11aS)-2-fluoro7-methoxy-2-nitrobenzoylpyrrolidin-2-carboxaldehydediethylthioactal]. VII (1060 mg, 1.0 mmol) was dissolved in methanol (20 ml) and added SnCl$_2$.2H$_2$O (2.25 mg, 10 mmol) was refluxed for 1.5 h. The reaction mixture was then carefully adjusted to pH 8 with saturated NaHCO$_3$ solution and then extracted with ethyl acetate (3×30 mL). The combined organic phase was dried over Na$_2$SO$_4$ and evaporated under vacuum to afford the crude. The 1,1'-{[(bispentane-1,N-diyl)piperazine]dioxy}bis (11aS)-2-fluoro-7-methoxy-2-aminobenzoylpyrrolidin-2-carboxaldehydediethylthioactal] (837 mg, 79%).

A solution of the 1,1'-{[(bispentane-1,N-diyl)piperazine] dioxy}bis(11aS)-2-fluoro-7-methoxy-2-aminobenzoylpyrrolidin-2-carboxaldehydediethylthioactal] of formula VIII (1000 mg, 1 mmol), HgCl$_2$ (1355 mg, 5 mmol) and CaCO$_3$ (500 mg, 5 mmol) in CH$_3$CN/H$_2$O (4:1,16 ml) was stirred at room temperature for 12 h until TLC (EtOAc), indicates complete loss of starting material. Then organic layer is evaporated in vacuum and the residue is diluted with EtOAc. To this saturated NaHCO$_3$ was added slowly at room temperature and the mixture is filtered through celite and washed with ethylacetate. The filterate is evaporated in vacuum to get crude 1,1'-{[(bispentane-1,N-diyl)piperazine]dioxy}bis [(11aS)-2-fluoro-7-methoxy-1,2,3,11a-tetrahydro-5H-pyrrolo[2,1-c][1,4]benzodiazepine-5-one], of formula IXc, which was further purified by column chromatography on silica gel eluting first with ethyl acetate to remove traces of mercuric salts and further eluted with CHCl$_3$-methanol (9:1) (560 mg, 56%).

$^1$H NMR (CDCl$_3$, 200 MHz): δ 1.44-2.09 (m, 12H), 2.30-2.51 (m, 4H), 2.52-3.0 (m, 8H), 3.47-3.87 (m, 10H), 3.93 (s, 6H), 4.0-4.1 (m, 4H), 5.27-5.58 (m, 2H), 6.9 (s, 2H), 7.49 (s, 2H), 7.9 (d, 2H, J=4.6 Hz).

EXAMPLE 4

A solution of (2S)—N-(4-hydroxy-5-methoxy-2-nitrobenzoyl)-4,4-difluoropyrrolidine-2-carboxaldehydediethylthioacetal IV (436 mmol), 1,3-dibromopropane (0.3 ml, 3 mmol) and K2CO3 (690 mg, 5 mmol) in dry acetone (40 ml) was refluxed for 48 h. After the completion of reaction as indicated by TLC, EtOAc-hexane (6:4), the reaction mixture was poured on to the water and then extracted with ethylacetate. Evaporation of the organic layer gave the crude product, which was further purified by column chromatography on silica gel eluting with EtOAc-hexane (1:1) gave the pure (2S)—N-[4-(4-bromopropoxy)-5-methoxy-2-nitrobenzoyl)-4,4-difluoropyrrolidine-2-carboxaldehydediethylthioacetal of formula V (370 mg, 85%).

$^1$H NMR (CDCl$_3$, 200 MHz): δ 1.36-1.42 (m, 6H), 2.39-2.47 (m, 2H), 2.62-2.95 (m, 6H), 3.48-3.58 (m, 2H), 3.64 (t, 2H, J=6.0 Hz), 3.96 (s, 3H), 4.26 (t, 2H, J=5.2 Hz), 4.82 (d, 1H), 4.89-4.96 (m, 1H), 6.77 (s, 1H), 7.72 (s, 1H) LCMS: m/z 580 (M$^+$+23).

A solution of (2S)—N-[4-(4-bromopropoxy)-2-nitrobenzoyl)-4,4-difluoro pyrrolidine-2-carboxaldehydediethylthioacetal of formula V. (557 mg, 1 mmol), piperazine (43 mg, 0.5 mmol) of the formula VI and K$_2$CO$_3$ (1380 ring, 10 mmol) in dry acetone (30 ml) was refluxed for 48 h. After the completion of reaction as indicated by TLC, EtOAc, the reaction mixture was on to the water and then extracted with ethylacetate. Evaporation of the organic layer gave the crude product, which was further purified by column chromatography on silica gel eluting with EtOAc-hexane (9:1) gave the pure 1,1'-{[(bispropane-1,N-diyl)piperazine]dioxy}bis(11aS)-2,2-difluoro7-methoxy-2-nitrobenzoylpyrrolidin-2-carboxaldehydediethylthioactal] (417 mg 75%).

$^1$H NMR (CDCl$_3$, 200 MHz): δ 1.25-1.39 (m, 12H), 2.0-2.14 (m, 4H), 2.58-2.66 (m, 8H), 2.69-2.88 (m, 12H), 3.45-3.79 (m, 8H), 3.94 (s, 6H), 4.1 (t, 4H), 4.78 (d, 2H), 4.85-4.96 (m, 2H), 6.7 (s, 2H), 7.6 (s, 1H) ESIMS: m/z 1039 (M$^+$).

The 1,1'-{[(bispropane-1,N-diyl)piperazine]dioxy}bis(11aS)-2,2-difluoro7-methoxy-2-nitrobenzoylpyrrolidin-2-carboxaldehydediethylthioactal]. VII (1039 mg, 1.0 mmol) was dissolved in methanol (20 ml) and added SnCl$_2$.2H$_2$O (2.25 mg, 10.0 mmol) was refluxed for 1.5 h. The reaction mixture was then carefully adjusted to pH 8 with saturated NaHCO$_3$ solution and then extracted with ethyl acetate (3×20 mL). The combined organic phase was dried over Na$_2$SO$_4$ and evaporated under vacuum to afford the crude. The 1,1'-{[(bispropane-1,N-diyl)piperazine]dioxy}bis (11aS)-2-2-difluoro-7-methoxy-2-aminobenzoylpyrrolidin-2-carboxaldehydediethylthioactal] (779 mg, 75%).

A solution of the 1,1'-{[(bispropane-1,N-diyl)piperazine]dioxy}bis(11aS)-2-2-difluoro-7-methoxy-2-aminobenzoylpyrrolidin-2-carboxaldehydediethylthioactal]. Of formula VIII (976 mg, 1.0 mmol), HgCl$_2$ (1355 mg, 5.0 mmol) and CaCO$_3$ (686 mg, 5.0 mmol) in CH$_3$CN/H$_2$O (4:1,16 ml) was stirred at room temperature for 12 h. Until TLC (EtOAc), indicates complete loss of starting material. Then organic layer is evaporated in vacuum and the residue is diluted with EtOAc. To this saturated NaHCO$_3$ was added slowly at room temperature and the mixture is filtered through celite and washed with ethylacetate. The filterate is evaporated in vacuum to get crude 1,1'-{[(bispropane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one], of formula XId, which was further purified by column chromatography on silica gel eluting first with ethyl acetate to remove traces of mercuric salts and further eluted with CHCl$_3$-methanol (9:1) (745 mg, 55%).

$^1$H NMR (CDCl$_3$, 200 MHz): δ 1.45-1.92 (m, 4H), 1.99-2.20 (m, 4H), 2.48-2.99 (m, 8H), 3.1-3.88 (m, 10H), 3.96 (s, 6H), 3.98-4.24 (m, 4H), 6.80 (s, 2H), 7.49 (s, 2H), 7.82 (d, 2H, J=3.8 Hz).

EXAMPLE 5

A solution of (2S)—N-(4-hydroxy-5-methoxy-2-nitrobenzoyl)-4,4-difluoro pyrrolidine-2-carboxaldehydediethylthioacetal IV (436, mg 1 mmol), 1,4-dibromobutane (0.35 ml, 3 mmol) and K$_2$CO$_3$ (690 mg, 5 mmol) in dry acetone (40 ml) was refluxed for 48 h. After the completion of reaction as indicated by TLC, EtOAc-hexane (6:4), the reaction mixture was poured on to the water and then extracted with ethylacetate. Evaporation of the organic layer gave the crude product, which was further purified by column chromatography on silica gel eluting with EtOAc-hexane (1:1) gave the pure (2S)—N-[4-(5-bromobutanoxy)-5-methoxy-2-nitrobenzoyl)-4,4-fluoropyrrolidine-2-carboxaldehydediethylthioacetal of formula V (353 mg, 81%).

$^1$H NMR (CDCl$_3$, 200 MHz): δ 1.28-1.40 (m, 6H), 2.0-2.5 (m, 4H), 2.58-2.79 (m, 6H), 3.51 (t, 2H), 3.75-(m, 2H), 3.96-(s, 3H), 4.10 (t, 2H), 4.79 (d, 1H), 4.85 (m, 1H), 6.74 (s, 1H) 7.6 (s, 1H) LCMS: m/z 594 (M$^+$+Na).

A solution of (2S)—N-[4-(5-bromobutanoxy)-5-methoxy-2-nitrobenzoyl)-4,4-fluoro pyrrolidine-2-carboxaldehydediethylthioacetal of formula V. (571 mg, 1 mmol), piperazine (43 mg, 0.5 mmol) of the formula VI and K$_2$CO$_3$ (1380 mg, 10 mmol) in dry acetone (40 ml) was refluxed for 48 h. After the completion of reaction as indicated by TLC, EtOAc, the reaction mixture was on to the water and then extracted with ethylacetate. Evaporation of the organic layer gave the crude product, which was further purified by column chromatography on silica gel eluting with EtOAc-hexane (9:1) gave the pure 1,1'-{[(bisbutane-1,N-diyl)piperazine]dioxy}bis(11aS)-2,2-difluoro7-methoxy-2-nitrobenzoylpyrrolidin-2-carboxaldehyddiethylthioactal] (485 mg, 85%).

$^1$H NMR (CDCl$_3$, 200 MHz): δ 1.33-1.48 (m, 12H), 1.66-1.98 (m, 8H), 2.40-2.50 (m, 8H), 2.63-2.94 (m, 12H), 3.42-3.83 (m, 8H), 3.92 (s, 6H), 4.11 (t, 4H), 4.77 (d, 2H), 4.83-4.94 (m, 2H), 6.72 (s, 2H), 7.62 (s, 2H) ESIMS: m/z 1067 (M$^+$).

The 1,1'-{[(bisbutane-1,N-diyl)piperazine]dioxy}bis(11aS)-2,2-difluoro7-methoxy-2-nitrobenzoylpyrrolidin-2-carboxaldehydediethylthioactal]. VII (1067 mg, 1.0 mmol) was dissolved in methanol (20 ml) and added SnCl$_2$.2H$_2$O (2.25 mg, 10.0 mmol) was refluxed for 1.5 h. The reaction mixture was then carefully adjusted to pH 8 with saturated NaHCO$_3$ solution and then extracted with ethyl acetate (3×20 mL). The combined organic phase was dried over Na$_2$SO$_4$ and evaporated under vacuum to afford the crude. The 1,1'-{[(bisbutane-1,N-diyl)piperazine]dioxy}bis(11aS)-2-2-difluoro-7-methoxy-2-aminobenzoylpyrrolidin-2-carboxaldehyde-diethylthioacetal] (810 mg, 76%).

A solution of the 1,1'-{[(bisbutane-1,N-diyl)piperazine]dioxy}bis(11aS)-2-2-difluoro-7-methoxy-2-aminobenzoylpyrrolidin-2-carboxaldehydediethylthioactal]. Of formula VIII (1007 mg, 1 mmol), HgCl$_2$ (1355 mg, 5.0 mmol) and CaCO$_3$ (500 mg, 5 mmol) in CH$_3$CN/H$_2$O (4:1,16 ml) was stirred at room temperature for 12 h. Until TLC (EtOAc), indicates complete loss of starting material. Then organic layer is evaporated in vacuum and the residue is diluted with EtOAc. To this saturated NaHCO$_3$ was added slowly at room temperature and the mixture is filtered through celite and washed with ethylacetate. The filterate is evaporated in vacuum to get crude 1,1'-{[(bisbutane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one], of formula IXe, which was further purified by column chromatography on silica gel eluting first with ethyl acetate to remove traces of mercuric salts and further eluted with CHCl$_3$-methanol (9:1) (523 mg, 52%).

$^1$H NMR (CDCl$_3$, 200 MHz): δ 1.56-1.94 (m, 8H), 1.99-2.35 (m, 4H), 2.49-2.99 (m, 8H), 3.29-3.87 (m, 10H), 3.93 (s, 6H), 3.98-4.37 (m, 4H), 6.89 (s, 2H), 7.46 (s, 2H), 7.83 (d, 2H, J=3.67).

EXAMPLE 6

A solution of (2S)—N-(4-hydroxy-5-methoxy-2-nitrobenzoyl)-4,4-difluoropyrrolidine-2-carboxaldehydediethylthioacetal IV (436 mg, 1 mmol), 1,5-dibromopentane (0.37 ml 3 mmol) and $K_2CO_3$ (1380 mg, 5 mmol) in dry acetone (40 ml) was refluxed for 48 h. After the completion of reaction as indicated by TLC, EtOAc-hexane (6:4), the reaction mixture was poured on to the water and then extracted with ethylacetate. Evaporation of the organic layer gave the crude product, which was further purified by column chromatography on silica gel eluting with EtOAc-hexane (1:1) gave the pure (2S)—N-[4-(6-bromopropoxy)-5-methoxy-2-nitro benzoyl]-4,4-fluoropyrrolidine-2-carboxaldehydediethylthioacetal of formula V (374 mg, 86%).

$^1$H NMR (CDCl$_3$, 200 MHz): δ 1.06-1.36 (m, 6H), 1.40-2.1 (m, 4H), 2.58-2.88 (m, 6H), 3.52 (t, 2H), 3.70-3.97 (m, 2H), 3.97 (s, 3H), 4.15 (t, 2H), 4.80 (d, 1H), 4.91-5.02 (m, 1H), 6.75 (s, 1H), 7.6 (s, 1H) LCMS: m/z 608 (M$^+$+Na).

A solution of (2S)—N-[4-(6-bromopentanoxy)-5-methoxy-2-nitrobenzoyl)-4,4-fluoropyrrolidine-2-carboxaldehydediethylthioacetal of formula V. (585 mg, 1 mmol), piperazine (43 mg, 0.5 mmol) of the formula VI and $K_2CO_3$ (1380 mg, 10 mmol) in dry acetone (40 ml) was refluxed for 48 h. After the completion of reaction as indicated by TLC, EtOAc, the reaction mixture was on to the water and then extracted with ethylacetate. Evaporation of the organic layer gave the crude product, which was further purified by column chromatography on silica gel eluting with EtOAc-hexane (9:1) gave the pure 1,1'-{[(bispentane-1,N-diyl)piperazine] dioxy}bis(11aS)-2,2-difluoro7-methoxy-2-nitrobenzoylpyrrolidin-2-carboxaldehydediethylthioactal] (462 mg, 79%).

$^1$H NMR (CDCl$_3$, 200 MHz): δ 1.34-1.40 (m, 12H), 1.47-1.96 (m, 12H), 2.36-2.49 (m, 4H), 2.50-2.66 (m, 8H), 2.68-2.90 (m, 8H), 3.37-3.80 (m, 8H), 3.94 (s, 6H), 4.08 (t, 4H), 4.77 (d, 2H), 4.85-4.91 (m, 2H), 6.72 (s, 2H), 7.63 (s, 2H) ESIMS: m/z 1095 (M$^+$).

The 1,1'-{[(bispentane-1,N-diyl)piperazine]dioxy}bis (11aS)-2,2-difluoro7-methoxy-2-nitrobenzoylpyrrolidin-2-carboxaldehydediethylthioactal]. VII (1095 mg, 1.0 mmol) was dissolved in methanol (20 ml) and added SnCl$_2$.2H$_2$O (2.25 mg, 10.0 mmol) was refluxed for 1.5 h. The reaction mixture was then carefully adjusted to pH 8 with saturated NaHCO$_3$ solution and then extracted with ethyl acetate (3×30 mL). The combined organic phase was dried over Na$_2$SO$_4$ and evaporated under vacuum to afford the crude. The 1,1'-{[(bispentane-1,N-diyl)piperazine]dioxy}bis(11aS)-2-2-difluoro-7-methoxy-2-aminobenzoylpyrrolidin-2-carboxaldehydediethylthioactal] (744 mg, 68%).

A solution of the 1,1'-{[(bispentane-1,N-diyl)piperazine] dioxy}bis(11aS)-2-2-di-fluoro-7-methoxy-2-aminobenzoylpyrrolidin-2-carboxaldehydediethylthioactal]. Of formula VIII (1035 mg, 1 mmol), HgCl$_2$ (1355 mg, 5 mmol) and CaCO$_3$ (500 mg, 5.0 mmol) in CH$_3$CN/H$_2$O (4:1,16 ml) was stirred at room temperature for 12 h. Until TLC (EtOAc), indicates complete loss of starting material. Then organic layer is evaporated in vacuum and the residue is diluted with EtOAc. To this saturated NaHCO$_3$ was added slowly at room temperature and the mixture is filtered through celite and washed with ethyl acetate. The filterate is evaporated in vacuum to get crude 1,1'-{[(bispentane-1,N-diyl)piperazine] dioxy}bis[(11aS)-2-2-difluoro-7-methoxy-1,2,3,11a-tetrahydro-5H-pyrrolo[2,1-c][1,4]benzo-diazepine-5-one], of formula IXf, which was further purified by column chromatography on silica gel eluting first with ethyl acetate to remove traces of mercuric salts and further eluted with CHCl$_3$-methanol (9:1) (569 mg, 55%).

$^1$H NMR (CDCl$_3$, 200 MHz): δ 1.54-2.03 (m, 12H), 2.22-2.47 (m, 4H), 2.50-2.73 (m, 8H), 3.35-3.85 (m, 10H), 3.94 (s, 6H), 3.97-4.26 (m, 4H), 6.71 (s, 2H), 7.47 (s, 2H), 7.79 (d, 2H J=3.6) ESIMS: m/z 787 (M$^+$+H).

Biological Activity: some of in vitro biological activity studies were carried out at the National Cancer Institute, Maryland, USA.

Cytotoxicity: The compounds (IXa) 1,1'-{[(bispropane-1, N-diyl)piperazine]dioxy}bis[(11aS)-2-fluoro-7-methoxy-1, 2,3,11a-tetrahydro-5H-pyrrolo[2,1-c][1,4]benzodiazepine-5-one] and (IXd) 1,1'-{[(bispropane-1,N-diyl)piperazine] dioxy}bis[(11aS)-2-2-difluoro-7-methoxy-1,2,3,11a-tetrahydro-5H-pyrrolo[2,1c][1,4]benzo diazepine-5-one].

The above compounds were evaluated for in vitro anticancer activity against sixty human tumor cells derived from nine cancer types (leukemia, non small cell cancer, colon cancer CNS cancer, melanoma, ovarian cancer renal cancer, prostate cancer and breast cancer) as per NCI protocol. For each compound, dose response curves for each cell line were measured at a minimum of five concentrations at 10-fold dilution. A protocol of 48 h continuous drug exposure was used, and a sulforhodamine B (SRB) protein assay was used to estimate cell viability or growth. The concentration causing 50% cell growth inhibition (GI50), total cell growth inhibition (TGI, 0% growth) and 50% cell death (LC-50% growth) compared with the control was calculated. The mean graph midpoint values of log$_{10}$ TGI and log$_{10}$ LC50 as well as log$_{10}$ GI50 for IXa and IXd are listed in table 1. As demonstrated by mean graph pattern compounds IXa and IXd are exhibit an interesting profile of activity and selectivity for various cell lines. The mean graph midpoint of log$_{10}$ TGI and log$_{10}$ LC50 showed similar pattern to the log$_{10}$ GI50 mean graph midpoints.

TABLE 1 log$_{10}$ GI50 log$_{10}$ TGI and log$_{10}$ LC50 mean graphs midpoint (MG_MID) of in vitro cytotoxicity data for the compounds IXa and IXd against human tumor cell lines.

| Compound | Log$_{10}$ GI50 | Log$_{10}$ TGI | Log$_{10}$ LC50 |
| --- | --- | --- | --- |
| IXa | −7.28 | −6.12 | −4.65 |
| IXd | −5.41 | −4.79 | −4.2 |

The in vitro anticancer activity for two representative compounds have given in table 2.

Among them IXa exhibits a wide spectrum of activity against fifty nine cell lines in nine cell panels, with GI50 value of <95 nM. In the leukemia cell line the growth of CCRF-CEM, HL-60 (TB), K-562, MOLT-4, RPMI-8226 and SR Cell lines were affected by the. Compound IXa with GI50 values as 10, 10, 15, 10, 22, 10.nM respectively. The GI50 values of compound IXa against non-small cell long cancer HOP-62, HOP 92, NCI-H23, NCI-H460, NCI-H522 cell lines are 12, 96, 32, 10, 10, nM respectively. The GI50 values of compound IXa against colon cancer COLO 205, hct-116, SW-620 cell lines are 40, 28, 56 nM respectively. The GI50 values of compound IXa against CNS cancer SF-268, SF-539, SNB-19, SNB-75 U251 11, 11, 28, 33, 15 nM respectively. The GI50 values of compound IXa against melanoma cancer LOX, MVI, MALME-3M, M14, SK-MEL-2, SK-MEL-28, UACC-62, 17, 24, 35, 43, 31, 26 nM respectively. The GI50 values of compound IXa against Ovarian cancer GI50 ROV1, OVCAR-3, SK-OV-3, are in 59, 48, 70 nM respectively. The GI50 values of compound IXa Renal cancer 786-o, A498, CAK-1, SN12C, 39, 66, 28, 18, nM respectively in prostate cancer cell of compound IX a values shows against PC-3, DU-145, 15, 47 nM respectively. And the GI50 values of compound IXa against Breast cancer MCF7, HS578T, MDA-MB-435, BT-549, T-47D, MDAMB-468 10, 48, 34, 95, 13, 10, nM respectively in this studies the compound IXd exhibited cytotoxicity activity against fifty nine cell lines is nine cancer cell panels with GI50 values are in a range of $9.79 \times 10^{-7}$-$8.64 \times 10^{-6}$ µM particularly in the compound IXd IG50 values against in leukemia cancer CCRF-CEM, SR, $9.79 \times 10$-7 µM and $8.82 \times 10$-7 µM the cytotoxicity of IXa and IXd in selected cancer cell lines have been illustrated in Table 2.

Table 2 the average GI50 values for each cancer panel of compounds IXa and IX d have been illustrated in table 2

TABLE 2 cytotoxicity of compound IX a and IX d in selected cancer cell lines.

| Cancer panel/cell line | GI$_{50}$ (nM) IX a | Cancer panel/cell line | GI$_{50}$ (µM) IX d |
|---|---|---|---|
| Leukemia | | Leukemia | |
| CCRF-CEM | 10 | CCRF-CEM | 0.9 |
| HL-60(TB) | 10 | HL-60(TB) | 1.18 |
| K-562 | 15 | K-562 | 1.7 |
| MOLT-4 | 10 | MOLT-4 | 2.02 |
| RPMI-8226 | 22 | RPMI-8226 | 2.20 |
| SR | 10 | SR | 0.8 |
| Non-small cell lung | | Non-small cell lung | |
| HOP-62 | 12 | A549/ATCC | 7.3 |
| HOP-92 | 96 | HOP-62 | 3.17 |
| NCI-H23 | 32 | HOP-92 | 6.14 |
| NCI-H460 | 10 | NCI-H322M | 1.96 |
| NCI-H522 | 10 | NCI-H460 | 2.60 |
| | | NCI-H522 | 1.14 |
| Colon | | Colon | |
| COLO 205 | 40 | COLO 205 | 3.09 |
| HCT-116 | 28 | HCC-2998 | 5.40 |
| SW-620 | 56 | HCT-116 | 3.59 |
| | | HT29 | 3.61 |
| | | KM12 | 4.10 |
| | | SW-620 | 2.61 |
| CNS | | CNS | |
| SF-268 | 11 | SF-268 | 3.57 |
| SF-539 | 11 | SF-539 | 3.0 |
| SNB-19 | 28 | SNB-19 | 4.08 |
| SNB-75 | 33 | SNB-75 | 5.52 |
| U251 | 15 | U251 | 3.36 |
| Melanoma | | Melanoma | |
| LOX IMVI | 17 | LOX IMVI | 1.89 |
| MALME-3M | 24 | MALME-3M | 2.80 |
| M14 | 35 | M14 | 3.25 |
| SK-MEL-28 | 43 | SK-MEL-28 | 4.28 |
| SK-MEL-5 | 31 | SK-MEL-5 | 1.86 |
| UACC-62 | 26 | UACC-62 | 3.05 |
| Ovarian | | Ovarian | |
| IGROV1 | 59 | IGROV1 | 1.92 |
| OVCAR-3 | 48 | OVCAR-3 | 3.55 |
| SK-OV-3 | 70 | OVCAR-5 | 3.83 |
| | | OVCAR-8 | 6.30 |
| | | SK-OV-3 | 8.64 |
| Renal | | Renal | |
| 786-0 | 39 | 786-0 | 3.17 |
| A498 | 66 | A498 | 2.43 |
| CAKI-1 | 28 | ACHN | 5.64 |
| SN12C | 18 | CAKI-1 | 3.31 |
| | | RXF 393 | 2.14 |
| | | SN12C | 4.05 |
| | | TK-10 | 4.38 |
| Prostate | | Prostate | |
| PC-3 | 15 | PC-3 | 3.06 |
| DU-145 | 47 | DU-145 | 3.63 |
| Breast | | Breast | |
| MCF7 | 10 | MCF7 | 2.09 |
| HS 578T | 48 | MDA-MB-231/ATCC | 4.29 |
| MDA-MB-435 | 34 | HS 578T | 2.94 |
| BT-549 | 95 | MDA-MB-435 | 1.95 |
| T-47D | 13 | BT-549 | 3.25 |
| MDA-MB-468 | 10 | T-47D | 1.38 |
| | | MDA-MB-468 | |

Thermal Denaturation Studies

The DNA binding affinity of the C2-Fluoro substituted piperazine linked pyrrolo[2,1c][1,4]benzodiazepine dimers were subjected to thermal denaturation studies using calf thymus (CT) DNA (Jones, G. B.; Davey, C. L.; Jenkins, T. C.; Kamal, A.; Kneale, G. G.; Neidle, S.; Webster, G. D.; Thurston, D. E. *Anti-cancer Drug Des.* 1990, 5, 249. McConnaughie, A. W.; Jenkins, T. C. *J. Med. Chem.* 1995, 38, 3488). The studies for these compounds (IXa-f) were carried out by DNA/ligand molar ratio is 1:5 the increase in the helix melting temperature ($\Delta T_m$) for each compound was examined at 0 h. The DNA biding activity for these novel C2-Fluoro substituted piperazine linked pyrrolo[2,1c][1,4]benzodiazepine dimers have been examined by thermal denaturation studies using calf thymus (CT) DNA melting studies shows that these compounds stabilize the $\Box T_m$ for CT-DNA at pH 7.0, incubated at 37° C., were PBD/DNA molar ratio is 1:5 interestingly, in this assay all compounds of fluoro substituted dimer (IXa-f) elevates the melting temperature CT-DNA by margin of 11-38° C. after incubation for at 37° C. Data for DSB-120 and SJG-136 are included in Table-3 for comparison. The synthetic DC-81 dimer (DSB-120) gives a $\Delta T_m$ 10.2° C. and SJC-136 gives a $\Box T_m$ of 25° C. under identical experimental condition.

TABLE 3

Thermaldenaturation data for C2-Fluoro substituted piperazine linked pyrrolo[2,1-c][1,4]benzodiazepine dimers with calf thymus (CT) DNA.

| | | $\Delta T_m$(° C.)$^a$ after incubation at 37° C. for |
|---|---|---|
| PBD Dimers | [PBD]:[DNA] molar ratio$^b$ | 0 h |
| IXa | 1:5 | 37.0 |
| IXb | 1:5 | 38.0 |
| IXc | 1:5 | 37.0 |
| IXd | 1:5 | 11.0 |
| IXe | 1:5 | 14.0 |
| IXf | 1:5 | 13.0 |
| DSB-120 | 1:5 | 10.2 |
| SJG-136$^c$ | 1:5 | 25.0 |

$^a$For CT-DNA alone at pH 7.00 $\Box$ 0.01, T$_m$ = 69.6° C. ± 0.01 (mean value from 10 separate determinations), all $\Delta T_m$ values are $\Box$ 0.1-0.2° C.

$^b$For a 1:5 molar ratio of [PBD]/[DNA], where CT-DNA concentration = 100 µM and ligand concentration = 20 µM in aqueous sodium phosphate buffer [10 mM sodium phosphate + 1 mM EDTA, pH 7.00 ± 0.01];

$^c$literature value of SJC-136

ADVANTAGES OF THE INVENTION

1. The present invention provides a C2-Fluoro substituted piperazine linked pyrrolo[2,1-c][1,4]benzodiazepine dimers useful as antitumour agents.

2. It also provides a process for the preparation of C2-Fluoro substituted piperazine linked pyrrolo[2,1-c][1,4]benzodiazepine dimers.

We claim:
1. A compound of formula IX

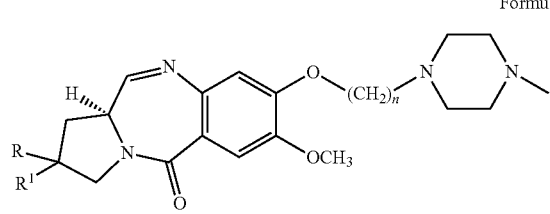

Formula IX

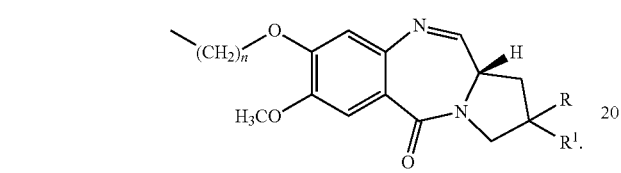

wherein R is F, R¹ is F or H and n = 3-10

2. A compound of claim 1 selected from the group consisting of:
1,1'-{[(bispropane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one] (IXa);
1,1'-{[(bisbutane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one] (IXb);
1,1'-{[(bispentane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one] (IXc);
1,1'-{[(bispropane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one] (IXd);
1,1'-{[(bisbutane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one] (IXe) and
1,1'-{[(bispentane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one] (IXf).

3. An in vitro method for inhibiting tumor cell growth or causing tumor cell death comprising administering a therapeutically effective amount of a compound of claim 1 to human cancer cell lines selected from the group consisting of lung, colon, breast, ovarian, leukemia, Renal, Melanoma, Prostate and CNS cell lines.

4. A process for the preparation of a compound of formula IX
and the said process comprising the step of:
(a) Preparing (2S)—N-(4-hydroxy-5-methoxy-2-nitrobenzoyl)-4-fluorinated-pyrrolidine-2-carboxaldehydediethylthioacetal of formula IV

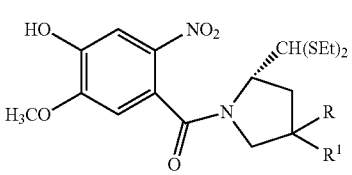

Formula IV

R = F and R¹ = F or H (b) reacting the compound of formula IV obtained in step (a) with dibromoalkane in a dry aprotic water miscible organic solvent, in the presence of mild inorganic base, under reflux, for a period up to 48 hours, purifying the resultant crude product to obtain the compound of (2S)—N-[4-n-bromoalkoxy)-5-methoxy-2-nitrobenzoyl]-4,fluorinated-pyrrolidine-2-carboxaldehydediethylthioacetal of formula V,

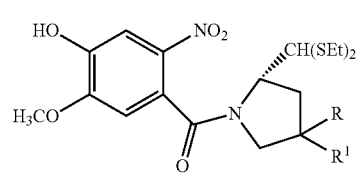

Formula V

R = F, R¹ = F or H, n = 3-10

(c) reacting the compound of formula V obtained in step (b) with piperazine in a dry aprotic water miscible organic solvent, in the presence of mild inorganic base, under reflux, for a period of 45-48 hours, followed by pouring the resultant reaction mixture on to the water and extracting and purifying the resultant crude product by known method to obtain the compound 1,1'-{[(bisalkane-1,N-diyl)piperazine]dioxy}bis(11aS)-2-fluorinated-7-methoxy-2-nitrobenzoylpyrrolidin-2-carboxaldehydediethylthioacetal] of formula VII Formula IX

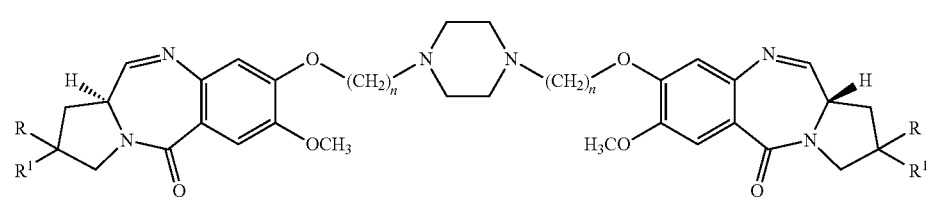

wherein R is F, R¹ is F or H and n = 3-10

Formula VII

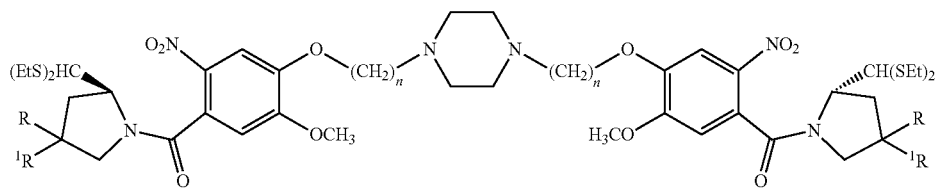

R = F, R¹ = F or H, n= 3-10

(d) reducing the compound of formula VII obtained in step (c) with $SnCl_2.2H_2O$ in an organic solvent, under reflux, for a period of 1-2 hours, at a pH of 8 in the presence of saturated alkali bicarbonate solution, followed by extraction with an organic solvent and drying the resultant organic phase over $Na_2SO_4$ and evaporating the solvent under vacuum to obtain the resultant compound. 1,1'-{[(bisalkane-1,N-diyl)piperazine]dioxy}bis (11aS)-2-fluorinated-7-methoxy-2-amino benzoylpyrrolidin-2-carboxaldehydediethylthioacetal] of formula VIII, 1,1'-{[(bispropane-1,N-diyl)piperazine]dioxy}bis(11aS)-2-2-difluoro-7-methoxy -2-nitrobenzoylpyrrolidin-2-carboxaldehydediethylthioacetal] (VIId);

1,1'-{[(bisbutane-1,N-diyl)piperazine]dioxy}bis(11aS)-2-2-difluoro-7-methoxy -2-nitrobenzoylpyrrolidin-2-carboxaldehyde diethylthioacetal] (VIIe) and 1,1'-{[(bispentane-1,N-diyl)piperazine]dioxy}bis(11aS)-2-2-difluoro-7-methoxy -2-nitrobenzoylpyrrolidin-2-carboxaldehydediethylthioacetal] (VIIf).

Formula VIII

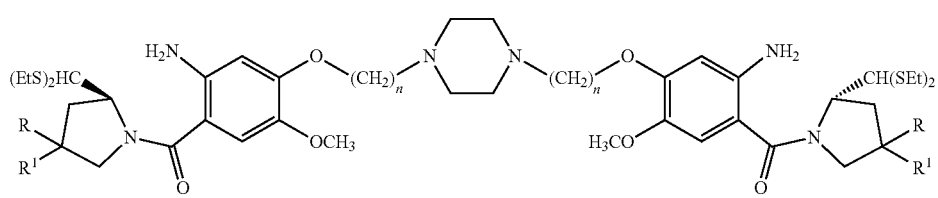

R = F, R¹= F or H, n= 3-10

(e) reacting the compound of formula VIII with mercurous chloride and calcium carbonate in the presence of an aqueous organic solvent wherein organic solvent to water ratio is about 4:1, under stirring, at a temperature of 25-30° C., for a period of about 12 hours, followed by the evaporation of organic layer to obtain the crude residue and purifying the residue to obtain the desired product of formula IX.

5. A process according to claim 4, wherein the dibromoalkane used in step (a) is selected from the group consisting of 1,3-dibromopropane, 1,4-dibromobutane and 1,5-dibromopantane.

6. A process according to claim 4, wherein the dry organic solvent used in step (b) and (c) is selected from the group consisting of acetone, acetonitrile and DMF.

7. A process according to claim 4, wherein the mild inorganic base used in step (b) and (c) is selected from the group consisting of $K_2CO_3$, $BaCO_3$ and $CsCO_3$.

8. A process according to claim 4 wherein the compound of formula VII used in step (c) is selected from the group consisting of 1,1'-{[(bispropane-1,N-diyl)piperazine]dioxy}bis(11aS)-2-fluoro-7-methoxy-2-nitrobenzoyl pyrrolidin-2-carboxaldehydediethylthioacetal] (VIIa);

1,1'-{[(bisbutane-1,N-diyl)piperazine]dioxy}bis(11aS)-2-fluoro-7-methoxy-2-nitrobenzoylpyrrolidin-2-carboxaldehydediethylthioacetal] (VIIb);

1,1'-{[(bispentane-1,N-diyl)piperazine]dioxy}bis(11aS)-2-fluoro-7-methoxy-2-nitrobenzoylpyrrolidin-2-carboxaldehydediethylthioacetal] (VIIc);

9. A process according to claim 4, wherein the compound of formula VIII obtained in step (d) is selected from the group consisting of 1,1'-{[(bispropane-1,N-diyl)piperazine]dioxy}bis(11aS)-2-fluoro-7-methoxy-2-aminobenzoylpyrrolidin-2-carboxaldehydediethylthioacetal] (VIIIa);

1,1'-{[(bisbutane-1,N-diyl)piperazine]dioxy}bis(11aS)-2-fluoro-7-methoxy-2-aminobenzoylpyrrolidin-2-carboxaldehydediethylthioacetal] (VIIIb);

1,1'-{[(bispentane-1,N-diyl)piperazine]dioxy}bis(11aS)-2-fluoro-7-methoxy-2-aminobenzoylpyrrolidin-2-carboxaldehydediethylthioacetal] (VIIIc);

1,1'-{[(bispropane-1,N-diyl)piperazine]dioxy}bis(11aS)-2-fluoro-7-methoxy-2-aminobenzoylpyrrolidin-2-carboxaldehydediethylthioacetal] (VIIId);

1,1'-{[(bisbutane-1,N-diyl)piperazine]dioxy}bis(11aS)-2-fluoro-7-methoxy-2-aminobenzoylpyrrolidin-2-carboxaldehydediethylthioacetal] (VIIIe) and 1,1'-{[(bispentane-1,N-diyl)piperazine]dioxy}bis(11aS)-2-fluoro-7-methoxy-2-aminobenzoylpyrrolidin-2-carboxaldehydediethylthioacetal] (VIIIf).

10. A process according to claim 4, wherein the organic solvent used in step (d) are ethyl acetate, chloroform and methanol.

11. A process according to claim 4, wherein the alkali bicarbonate of step (d) is sodium bicarbonate.

12. A process according to claim 4, wherein the organic solvent used in step (d) is methanol.

13. A process according to claim 4, wherein the organic solvent used in step (e) is acetonitrile.

14. A process according to claim 4, wherein the compound of formula IX obtained in step (e) is selected from the group consisting of:

1,1'-{[(bispropane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one] (IXa);

1,1'-{[(bisbutane-1,N-diyl)piperazine]dioxy}bis[(11aS)-2-fluoro-7-methoxy-1,2,3,11a-tetrahydro-5H-pyrrolo[2,1-c][1,4]benzodiazepine-5-one] (IXb);

1,1'-{[(bispentane-1,N-diyl)piperazine]dioxy}bis[(11aS)-2-fluoro-7-methoxy-1,2,3,11a-tetrahydro-5H-pyrrolo[2,1-[1,4]benzodiazepine-5-one] (IXc);

1,1'-{[(bispropane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one] (IXd);

1,1'-{[(bisbutane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one](IXe) and 1,1'-{[(bispentane-1,N-diyl)piperazine]dioxy}bis[(11aS)-2-2-difluoro-7-methoxy-1,2,3,11a-tetrahydro-5H-pyrrolo[2,1-c][1,4]benzodiazepine-5-one] (IXf).

15. A pharmaceutical composition comprising an effective amount of 1,1'-{[(bisalkane-1,N-diyl) piperazine]dioxy}bis[(11aS)-2-fluoro-7-methoxy-1,2,3, 11a-tetrahydro-5H-pyrrolo[2,1-c][1,4]benzodiazepine-5-one] or 1,1'-{[(bisalkane-1,N-diyl) piperazine]bis(11aS)-2-2-difluoro-7-methoxy-1,2,3,11a-tetrahydro-5H-pyrrolo[2,1-c][1,4]benzodiazepine-5-one optionally along with pharmaceutically acceptable additives.

* * * * *